(12) United States Patent
Winde et al.

(10) Patent No.: US 8,703,985 B2
(45) Date of Patent: Apr. 22, 2014

(54) METHOD FOR PREPARATION OF RUTHENIUM-INDENYLIDENE CARBENE CATALYSTS

(75) Inventors: Roland Winde, Frankfurt (DE); Ralf Karch, Kleinostheim (DE); Andreas Rivas-Nass, Schriesheim (DE); Angelino Doppiu, Seligenstadt (DE); Gerhard Peter, Freigericht (DE); Eileen Woerner, Maintal (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 299 days.

(21) Appl. No.: 13/122,248

(22) PCT Filed: Oct. 2, 2009

(86) PCT No.: PCT/EP2009/007072
§ 371 (c)(1),
(2), (4) Date: Apr. 1, 2011

(87) PCT Pub. No.: WO2010/037550
PCT Pub. Date: Apr. 8, 2010

(65) Prior Publication Data
US 2011/0190524 A1 Aug. 4, 2011

(30) Foreign Application Priority Data
Oct. 4, 2008 (EP) .................................. 08017438

(51) Int. Cl.
*C07F 15/00* (2006.01)
(52) U.S. Cl.
USPC ........................................ 556/21; 556/136
(58) Field of Classification Search
USPC ................................................. 556/21, 136
See application file for complete search history.

(56) References Cited

U.S. PATENT DOCUMENTS

| | | |
|---|---|---|
| 5,312,940 A | 5/1994 | Grubbs et al. |
| 5,831,108 A | 11/1998 | Grubbs et al. |
| 7,671,224 B2 | 3/2010 | Winde et al. |

FOREIGN PATENT DOCUMENTS

WO 2007/010453 1/2007

OTHER PUBLICATIONS

Shaffer et al., Journal of Organometallic Chemistry, vol. 692, pp. 5221-5233 (published online Aug. 11, 2007).*
Jafarpour et al., Organometallics, vol. 18, No. 23, pp. 5416-5419 (1999).*
International Search Report for PCT/EP2009/007072 mailed Feb. 5, 2010.

Helmut Werner, et al., "Methyliodid als Quelle für CH₂: zwei Wege zur Erzeugung 1, 1-disubstituierter Butatriene in der Koordinationssphäre eines Übergangsmetalls", Angew. Chem, 1996, vol. 108, nr. 11, pp. 1330-1332.
Daniel Touchard, et al., "Metallacumulenes: Activation of Diynes and Formation of New Allenylideneruthenium Complexes. Crystal Structures of . . . Derivatives", American Chemical Society, Organometallics, 1995, vol. 14, No. 11, pp. 5263-5272.
Ricardo Castarlenas, et al., "Allenylidene-to-Indenylidene Rearrangment in Arene-Ruthenium Complexes: A Key Step to Highly Active Catalysts for Olefin Metathesis Reactions", J. Am. Chem. Soc., 2006, vol. 128, pp. 4079-4089.
John P. Selegue, "Synthesis and Structure of . . . Complex", American Chemical Society, Organometallics, 1982, vol. 1, pp. 217-218.
Lutz Ackermann, et al., "Ruthenium Carbene Complexes with Imidazolin-2-ylidene Ligands . . . RCM", Elsvier Science Ltd., Tetrahedron Letters, 1999, vol. 40, pp. 4787-4790.
M. Mark Midland, "Preparation of Monolithium Acetylide in Tetrahydrofuran, Reaction with Aldehydes and Ketones", J. Org. Chem., 1975, vol. 40, No. 15, pp. 2250-2252.
Alois Fürstner, et al., "Total Synthesis and Structural Refinement of the Cyclic Tripyrrole Pigment Nonylprodigiosin", J. Org. Chem, 1999, vol. 64, pp. 8275-8280.
Alois Fürstner, et al., "Coordinatively unsaturated ruthenium allenylidene complexes: highly effective, well defined catalysts for the ring-closure metathesis of α,ω-dienes and dienynes", Chem. Commun., 1999, pp. 601-602.
Fabien Boeda, et al., "Ruthenium-indenylidene complexes: powerful tools for metathesis transformations", Chem. Commun., 2008, pp. 2726-2740.
Stijin Monsaert, et al., "Indenylidene-Ruthenium Compleaxes Bearing . . . Reactions", Eur. J. Inorg. Chem, 2008, pp. 432-440.
Karsten J. Harlow, et al., "The first co-ordinatively un saturated Group 8 allenylidene complexes: insights into Grubbs' vs. Dixneuf-Fürstner olefin metathesis catalysts", J. Chem. Soc., Dalton Trans., 1999, pp. 285-291.
Alois Fürstner, et al., "Indenylidene Complexes of Ruthenium: Optimized . . . Nakadomarin A", Chem. Eur. J., 2001, vol. 7, No. 22, pp. 4811-4820.
Erika A. Shaffer, et al., "Synthesis of ruthenium phenylindenylidene . . . investigation", Journal of Organomettallic Chemistry, 2007, vol. 692, pp. 5221-5233.
Reto Dorta, et al., "Cross Metathesis Allowing the Conversion of Ruthenium . . . Catalyst", Adv. Synthesis Catal., 2004, vol. 346, pp. 917-920.
P. S. Hallman, et al., "Tetrakis (Triphenylphosphine) Dichlororuthenium (II) . . . ", Inorganic Syntheses, 1970, chapter 40, pp. 237-240.

* cited by examiner

*Primary Examiner* — Porfirio Nazario Gonzalez
(74) *Attorney, Agent, or Firm* — Smith, Gambrell & Russell, LLP

(57) ABSTRACT

The present invention is directed to a method for the preparation of ruthenium indenylidene carbene catalysts of the type (L)(L')X₂Ru(II)(aryl-indenylidene). The method comprises the steps of reacting the precursor compound $Ru(PPh_3)_nX_2$ (n=3-4) with a propargyl alcohol derivative in an cyclic diether solvent such as 1,4-dioxane at temperatures in the range of 80 to 130° C. and reaction times of 1 to 60 minutes. Optionally, additional neutral electron donor ligands such as $PCy_3$, phobane ligands or NHC ligands are added to the reaction mixture for ligand exchange. The method includes a precipitation step for purification, after which the product is isolated. The ruthenium-indenylidene carbene catalysts are obtained in high purity and are used as catalysts for metathesis reactions (RCM, ROMP and CM) and as precursors for the synthesis of modified ruthenium carbene catalysts.

25 Claims, No Drawings

US 8,703,985 B2

METHOD FOR PREPARATION OF RUTHENIUM-INDENYLIDENE CARBENE CATALYSTS

The present invention relates to the preparation of ruthenium carbene catalysts for metathesis, in particular to the synthesis of ruthenium indenylidene carbene catalysts of the type (L)(L')X$_2$Ru(II)(aryl-indenylidene), in which the Ru=CR$_2$ carbene group is part of a bicyclic indenyl ring system. These catalysts are useful in a variety of olefin metathesis reactions and as precursors for the synthesis of other ruthenium carbene catalyst types. The method of the present invention is simple, environmentally friendly and yields products of high purity.

Olefin metathesis is a fundamental catalytic reaction and one of the most versatile ways to design new molecules by formation and rearrangement of carbon-carbon multiple bonds. The metathesis reactions help not only in significantly shortening synthetic pathways towards defined target molecules, but also give access to new applications not being feasible with the traditional means of organic chemistry. Various classes of metathesis reactions are known, such as, for example, ring-closing metathesis (RCM), ring-opening metathesis polymerization (ROMP) or cross metathesis (CM). In the past years, metathesis has become a widely used method for the formation of carbon-carbon bonds in organic synthesis and polymer chemistry.

The development of well-defined ruthenium-based carbene catalysts by Schrock and Grubbs has led to a fast growth in the field of metathesis. More and more, metathesis reactions are applied and integrated in the synthesis design of organic compounds, leading to an increased usage of metathesis catalysts in industrial laboratories. This trend is about to continue in the forthcoming years.

One of the first catalysts showing high activity, low sensitivity against functional groups as well as sufficient stability, were Grubbs "first generation" catalysts, especially (PCy$_3$)$_2$Cl$_2$Ru=CR$_2$, with CR$_2$ being CHPh. These catalysts are characterized by a penta-coordinated Ru(II) metal center bearing two phosphine ligands, two chloride ligands and a non-cyclic alkylidene group. These catalysts found fast acceptance in the organic synthesis community.

This catalyst family was followed by a "second generation" catalyst development, in which N-heterocyclic carbene ("NHC") ligands replace one phosphine ligand. In the meantime, a complete range of different metathesis catalysts, each offering specific features and properties are available on the market.

Over the past years, a specific class of metathesis catalysts, so-called Ruthenium-indenylidene carbene catalysts have gained increased importance. These types of Ru-carbene catalysts contain the Ru atom in the formal oxidation state +II; they are predominantly penta-coordinated and comprise a bicyclic indenylidene ring where the carbene C-atom in the indenylidene moiety is part of a bicyclic, condensed ring system.

These complexes exhibit the following general structure (FIG. 1)

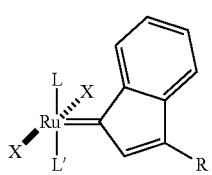

Figure 1

In FIG. 1, L and L' are representing, independent from another, neutral two-electron donor ligands. Examples are phosphine ligands such as PPh$_3$, PCy$_3$, phospha-bicyclononane (so-called "phobane") ligands such as 9-cyclohexyl-9-phospha-bicyclo-[3.3.1.]-nonane, 9-isobutyl-9-phos-pha-bicyclo-[3.3.1.]-nonane, 9-eicosyl-9-phosphabicyclo-[3.3.1.]-nonane, as well as N-heterocyclic carbene ("NHC") ligands such as unsaturated 1,3-bis(mesityl)-imidazoline-2-ylidene ("I-Mes"), saturated 1,3-bis (mesityl)-imidazolidine-2-ylidene ("S-IMes") or unsaturated 1,3-bis(2,6-diisopropylphenyl)-imidazoline-2-ylide ("IPr"), X is representing anionic halogenide ions (such as fluoride, chloride, bromide or iodide ions) and R is representing an aryl, phenyl or substituted phenyl group. Ruthenium complexes wherein the metathesis active carbene group (in the M=C<moiety) is a phenylindenylidene group, are preferred. Optionally, there can be an additional ligand present in these complexes to effect a hexa-coordination at the Ru-metal center. This additional ligand could be any neutral electron donor ligand such as pyridine, dioxane etc. In addition, one of the ligands L or L' and one of the ligands X may be bound together and as such may form a chelating monoanionic ligand.

The Ru-indenylidene catalysts exhibit a unique application profile in metathesis reactions (see for example F. Boeda, H. Clavier, S. P. Nolan, Chem. Commun. 2008, 2726-2740 and S. Monsaert, R. Drozdzak, V. Dragutan, I. Dragutan, F. Verpoort, Eur. J. Inorg. Chem., 2008, 432-440) and may allow for a reduction of catalyst loading in some applications. The catalysts exhibit improved thermal stability (ref to S. Monsaert, R. Drozdarek et al., Eur. J. Inorg. Chem. 2008, 432-440), and gain more and more importance in metathesis applications. Thus, for the industrial use of these catalyst materials, optimized manufacturing processes are required.

Despite considerable research in the field, the ruthenium-based catalysts presently in use are expensive. Hazardous chemicals, such as diazo reagents (e.g. diazoalkenes) are used in the preparation of standard ruthenium carbene complexes. Furthermore, the yields and the purity of the resulting catalyst products need to be improved.

U.S. Pat. No. 5,312,940 describes the preparation of Ru carbene complexes by the reaction of (PPh$_3$)$_3$RuCl$_2$ with reactants such as cyclopropenes or phosphoranes.

In U.S. Pat. No. 5,831,108, the preparation of Ru carbene complexes using diazo compounds having the general formula RC(N$_2$)R$^1$ is disclosed.

In early 1998, the first Ru-indenylidene complex (PPh$_3$)$_2$Cl$_2$Ru(3-phenylindenylidene) was obtained by reacting (PPh$_3$)$_3$RuCl$_2$ with 1,1-Diphenyl-propargyl-alcohol in refluxing THF (ref to K. J. Harlow, A. F. Hill et al., J. Chem. Soc. Dalton Trans., 1999, 285-291). It was first believed that the reaction would provide the corresponding allenylidene complex (PPh$_3$)$_2$Cl$_2$Ru=C=C=CPh$_2$. However, it was found later by Fuerstner et al. that the structure of this complex was not an allenylidene complex; instead it was re-arranged to an "indenylidene" complex (ref to Fuerstner et al, Chem. Eur. J. 2001, 7, No. 22, 4811-4820). Fuerstner described an optimized preparation method, based on the reaction of (PPh$_3$)$_3$RuCl$_2$ with 1,1-diphenyl-propargylalcohol in refluxing THF for 2.5 hours. Due to the long reaction time employed in this method, side products (primarily phosphine oxides) are formed.

Recently, the synthesis of ruthenium phenylindenylidene complexes was investigated in detail by E. A. Shaffer, H.-J. Schanz et al. in J. Organomet. Chem. 692, 5221-5233 (2007). The reaction of (PPh$_3$)$_{3-4}$RuCl$_2$ with 1,1-diphenyl-2-propyn-1-ol ("diphenylpropargylalcohol") was conducted in refluxing THF for 1.5 hours to produce the $(PPh_3)_2Cl_2Ru(phenyl-indenylidene)$ complex. By acid catalysis (i.e. by addition of acetylchloride ($CH_3COCl$) to the reaction), improved yields and high purity products were reported. However, it was found by the present inventors that, even if acid catalysis is employed, the preparation method according to Shaffer et al. still leads to impure catalyst products, which contain, among others, dimeric compounds.

In WO 2007/010453, the preparation of a Ru-indenylidene complex is disclosed, which carries two cyclohexylphobane ligands (mixture of two isomers 9-cyclohexyl-9-phosphabicyclo-[3.3.1.]-nonane. The preparation of this complex is conducted in refluxing THF in a sequential mode (indenylidene ring formation in refluxing THF, followed by ligand exchange).

R. Dorta, R. A. Kelly III and S. P. Nolan, *Adv. Synth. Catal.* 2004, 346, 917-920 describe the synthesis of $(PCy_3)_2Cl_2Ru$ (3-phenylindenylidene) by reaction of $(PPh_3)_3RuCl_2$ with 1,1-diphenyl-2-propyn-1-ol in refluxing THF, followed by a ligand exchange reaction of the resulting $(PPh_3)_2Cl_2Ru(3-phenylindenylidene)$ complex with $PCy_3$ in the same solvent by stirring overnight at room temperature. The complex is isolated by removing the volatiles and suspending the residues in diethylether. Thereafter the product is filtered and washed frequently with low boiling, hazardous solvents such as diethylether and pentane. This procedure is very time-consuming, expensive, and yields a product in low purity. Due to the long reaction time employed, the amount of side products is quite high. This method is therefore not suitable for industrial scale manufacturing.

Typically, in the state of the art, the indenylidene ring formation is conducted in tetrahydrofuran (THF) solvent under refluxing conditions, resulting in reaction temperatures around the boiling point of this solvent (i.e. 64 to 67° C.) and reaction times of 1.5 to 2.5 hours. Thereafter, a ligand exchange reaction is conducted in chlorinated solvents (typically dichloromethane or chloroform) at room temperature (i.e. 20 to 25° C.). Due to the long reaction times applied, the amount of impurities and side products is increasing. Furthermore, as the currently known procedures do not comprise a specific purification step (other than washing the residual material with solvent), the impurities are not efficiently removed from the final product. These impurities (dimeric compounds, phosphine oxides etc) may lead to performance losses of the resulting catalyst product, such as lower activity, higher catalyst consumption and lower turn-over numbers (TON). In summary, the currently known preparation methods for Ru-indenylidene complexes are lengthy, comprise long reaction times, yield low purity products and are, due to the fact that the solvents are in most cases evaporated to dryness, not applicable to industrial production scale.

It was therefore an objective of the present invention to provide an improved method for preparation of Ru-indenylidene carbene catalysts. The method should be simple, straightforward and easily scalable; it should facilitate short reaction times and yield the Ru-indenylidene complexes in high purity and good yields, preferably in a single step ("one-pot") reaction. Furthermore, the method should be based on the use of non-hazardous solvents and should be environmentally friendly, inexpensive and applicable to industrial production.

The present invention provides a method for the preparation of a ruthenium-indenylidene carbene catalyst of the Formula 1

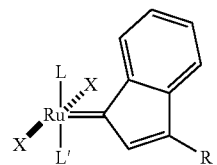

in which
Ru is penta-coordinated in the formal oxidation state +II,
X are anionic ligands such as $F^-$, $Cl^-$, $Br^-$ and $I^-$,
L or L' are, independent from each other, neutral electron donor ligands such as $PPh_3$, $PCy_3$, phobane ligands, NHC ligands or mixtures thereof,
R is an aryl, phenyl or substituted phenyl group,
said method comprising the steps of
a) reacting the precursor compound $Ru(PPh_3)_nX_2$ (n=3-4) with a propargyl alcohol derivative of the formula phenyl-$C(R)(OH)$—$C\equiv C$—H in a reaction mixture with a cyclic diether solvent at a temperature in the range of 80 to 130° C.,
b) optionally adding a neutral electron donor ligand L or L' (with the exemption of $PPh_3$) to the reaction mixture, and
c) precipitating the resulting ruthenium-indenylidene carbene catalyst from said reaction mixture.

The method may optionally further comprise at least one filtration step for separating the ruthenium indenylidene carbene catalyst from the reaction mixture as well as additional washing and/or drying steps.

In the first embodiment of the method of the present invention, Ru-aryl-indenylidene carbene complexes of the type shown in Formula 1a are prepared.

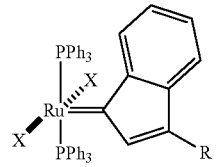

Formula 1a

In this first embodiment, the precursor compound $Ru(PPh_3)_nX_2$ (n=3-4) is reacted with the propargyl alcohol derivative of the type phenyl-$C(R)(OH)$—$C\equiv C$—H in the cyclic diether solvent and reaction step b) is omitted. No additional neutral electron donor ligand L or L' is added to the reaction mixture for ligand exchange. The resulting Ru-indenylidene carbene complex contains two $PPh_3$ ligands and is separated from the reaction mixture by a simple precipitation process from solution.

In the second embodiment of the present invention, reaction step b) is embraced and a neutral electron donor ligand (i.e. a ligand listed in the group L and/or L', however with the exemption of $PPh_3$) is added to the reaction mixture. After this step, which comprises an exchange of the ligand $PPh_3$ by a neutral electron donor ligand, the resulting product is again separated from the reaction mixture by a precipitation process from solution. This second embodiment enables the simple and fast preparation of Ru-aryl-indenylidene carbene complexes comprising various or mixed electron donor ligands L and/or L' in a "one-pot" reaction. As an example, $(PCy_3)_2Cl_2Ru(phenyl-indenylidene)$ is synthesized in a single step from $Ru(PPh_3)_nX_2$ (n=3-4) without the prior isolation of the intermediate (PPh₃)₂Cl₂Ru(phenyl-indenylidene) and obtained after the precipitation step c) in high purity.

It was found by the inventors of the present invention that, when conducting the indenylidene ring formation at higher temperatures in the range of 80 to 130° C. as described above, the reaction time for the ring formation is significantly shortened. Reaction times in the range of 1 to 60 minutes, preferably in the range of 1 to 30 minutes and most preferred, in the range of 1 to 15 minutes are possible. By this measure, the formation of undesired impurities (phosphine oxides, dimeric compounds etc.) is reduced, resulting in a product with significantly higher purity. In addition, high yields are obtained.

It was further found by the inventors that cyclic diether solvents with higher boiling points and a specific polarity range are advantageously used for the method of the present invention. The cyclic diether solvents having a polarity in a medium to low range affect a reduced solubility of the reaction product in the reaction mixture and thus enable the precipitation/crystallisation of the catalyst product by itself upon cool-down and/or concentration of the reaction mixture.

For the polarity of an organic solvent, generally the electrical dipole moment (given in Debye (D); 1 D=3.33564× $10^{-30}$ Cm) is taken in account. Generally, for best results, the cyclic diether solvent should have a medium to low dipole moment, preferably in the range of about 0.3 to 1.7 Debye. Solvents with higher dipole moments may keep the Ru-indenylidene complexes in solution; solvents with lower dipole moments do not sufficiently dissolve the reagents. The polarity of tetrahydrofurane (THF), a cyclic mono-ether commonly used in the prior art is too high, thus this solvent does not enable the precipitation/crystallisation step of the present invention.

Suitable cyclic diether solvents should have boiling points in the range of 80 to 130° C., preferably in the range of 85 to 120° C. at ambient pressure (normal pressure, 1 atm). By use of these cyclic diether solvents, higher reaction temperatures and shorter reaction times compared to the prior art are feasible.

Suitable cyclic diether solvents are 1,3-dioxane (boiling point 105-106° C.), 1,4-dioxane (boiling point 100-102° C.), 5-methyl-1,3-dioxane (boiling point about 114° C.) as well as mixtures thereof. Preferred cyclic diether solvents are 1,3-dioxane or 1,4-dioxane, the most preferred solvent is 1,4-dioxane. Additional co-solvents (such as THF etc.) may be added as long as the boiling point/boiling range of the resulting mixture is in the specified range of 80 to 130° C. and the polarity of the solvent mixture is not affected.

For the method of the present invention, substituted propargylalcohols of the type phenyl-(R)C(OH)—C≡C—H are employed. In this formula, R represents an aryl, a phenyl or a substituted phenyl group. 1,1-diphenyl-2-propyn-1-ol having the structure (phenyl)₂C(OH)—C≡C—H is preferred. This chemical compound is readily available on the market. Generally, the purity of the propargylalcohol compounds should be >95%. For best results, the propargylalcohol component is added in a slight excess to the reaction mixture (i.e. in quantities of 1.1 to 1.4 equivalents based on the Ru precursor).

As described by Shaffer et al., the allenylidene-indenylidene rearrangement is acid catalyzed. Thus, for improved results, step a) of the method of the present invention should be conducted in the presence of an acidic compound. Preferably, protic acids such as HCl, HBr, HI, H₂SO₄ or HNO₃ etc are used. These acids can be added in quantities of 1 to 1.5 equivalents to the reaction mixture. In a preferred version of the present invention, the acidic compound (i.e. the protic acid) is dissolved in the same cyclic diether solvent, which is used as solvent in the present invention and then added to the reaction mixture. A preferred acidic compound is HCl/dioxane solution, as commercially available from various vendors (for example 4M HCl solution in dioxane from Sigma-Aldrich GmbH, Munich). However, other acids, such as HBF₄ or triflic acid (CF₃SO₃H) may also be employed.

As ruthenium precursor compounds, Ru(II) complexes of the type Ru(PPh₃)ₙX₂ (n=3-4) are employed, wherein X represents anionic ligands, such as the halogenide anions fluoride (F⁻), chloride (Cl⁻), bromide (Br⁻), iodide (I⁻) or mixtures thereof. A preferred Ru(II) precursor is dichloro-tris-(triphenylphosphine)ruthenium(II) [(Ru(PPh₃)₃Cl₂)], wherein n=3. This complex is commercially available from various vendors. The Ru-content of this compound should be >9 wt. % Ru (the theoretical Ru-content is 10.54 wt %); small amounts of additional phosphine ligand PPh₃ may be present (ref to P. S. Hallman et al., *Inorganic Synthesis*, 12, (1970), 237-245).

Preferably, glass reactors or flasks with condenser and stirrer are used for the method of the present invention. The reactors may be flushed with dry inert gas (argon, nitrogen) prior to use. After charging the reactor with the reactants, the reactants are heated up and reaction step a) is conducted at the conditions given above (i.e. temperatures in the range of 80 to 130° C., preferably in the range of 85 to 120° C.; reaction times are the range of 1 to 60 minutes, preferably in the range of 1 to 30 minutes, most preferred in the range of 1 to 15 minutes).

Thereafter, in case reaction step b) is employed, an additional neutral electron donor ligand L and/or L' (with the exemption of PPh₃) is added to the reaction mixture. To facilitate the ligand exchange, a slight excess of additional ligand is recommended (about 2.2 to 3 equivalents in the case that two PPh₃ ligands are exchanged). Preferred additional ligands L/L' are tricyclohexylphosphine (PCy₃), phobane ligands or NHC ligands such as unsaturated 1,3-bis(mesityl)-imidazoline-2-ylidene ("I-Mes"), saturated 1,3-bis(mesityl)-imidazolidine-2-ylidene ("S-IMes") or unsaturated 1,3-bis-(2,6-diisopropylphenyl)-imidazoline-2-ylide ("IPr"). During step b), the reaction temperature may be maintained at the specified range of 80 to 130° C.; however, depending on the ligand type added, lower temperatures in the range of 60 to 130° C. may be employed. Typically, the reaction times for step b) are in the range of 15 mins to 6 hours.

In the case that reaction step b) is employing various electron donor ligands L and/or L', the addition of such ligands to the reaction mixture may be conducted simultaneously or sequentially, depending on the ligand types used. When strongly basic ligands, such as NHC ligands are employed, it is advantageous to remove the acidic compound (i.e. HCl, etc) from the reaction mixture prior to the addition of such ligands, for example by vacuum distillation. The amount of cyclic diether solvent removed in such vacuum operation may be replaced by other suitable solvents. As an example, the compound (PCy₃)(S-IMes)Cl₂Ru(phenylindenylidene) can be prepared by a sequential addition of the ligands L=PCy₃ and L'=S-IMes to the reaction mixture in reaction step b).

After the formation of the Ru-indenylidene carbene complex in step a) and optional step b), the reaction mixture is cooled down to temperatures in the range of 20 to 40° C., thereby initiating the precipitation of the product from the reaction mixture. If appropriate, the reaction mixture may additionally be concentrated prior to the precipitation/crystallisation step. For this purpose, the cyclic diether solvent is partly removed from the reaction mixture. Amounts up to 80 to 90% of the initial solvent quantity may be distilled off, for example by vacuum distillation. Alternatively, suitable solvent(s) with high or low polarity may be added to the reaction mixture to support the precipitation.

The method of the present invention may further comprise at least one step for separating the precipitated catalyst from the reaction mixture, such as filtration, centrifuging or decanting. Furthermore, additional washing and/or drying steps may be employed. Such procedures are standard methods and well known to the person skilled in the art. For washing or rinsing of the final catalyst product, solvents such as methanol or ethanol are preferred.

Due to the preparation method of the present invention, the resulting Ru-indenylidene catalysts reveal a high product quality, in particular a high purity. Furthermore, due to the fact that easily scaleable precipitation processes are employed, the preparation method is applicable to industrial production scale, The catalysts of the present invention are useful in a variety of olefin metathesis reactions such as ring-closing metathesis (RCM), ring-opening metathesis polymerization (ROMP) and cross metathesis (CM). Furthermore, they are valuable precursors for the synthesis of other, further modified ruthenium carbene catalysts.

Purity Analysis:

For purity determination of the P-containing Ru-indenylidene catalysts of the present invention, $^{31}$P-NMR spectroscopy is applied. The $^{31}$P-NMR spectra are recorded on a BRUKER DRX 500 NMR spectrometer at 200 MHz with complete proton decoupling at about 25° C. The chemical shifts of the phosphorus resonances are determined relative to phosphoric acid as an external standard ($H_3PO_4$: δ=0.0 ppm). The compounds are dissolved in a deuterated solvent ($CD_2Cl_2$). For quantitative determination of purity, the peak integration method is employed. Typically, the purity of the Ru-indenylidene catalysts prepared according to the invention is ≥90%, preferably ≥95% (as determined by $^{31}$P-NMR spectroscopy).

The invention is further described in the following examples without restricting its scope of protection.

EXAMPLE 1

Preparation of $(PPh_3)_2Cl_2Ru(phenylindenylidene)$

A one liter glass reactor with condenser and stirrer is filled with argon and thereafter with 800 ml of 1,4-dioxane. The solvent is heated up to 90° C.

Then, 29.3 g (140 mmol) of 1,1-diphenyl-2-propyn-1-ol (diphenylpropargylalcohol, GFS Chemicals Inc., Powell, Ohio, USA) and 120 g (120 mmol) of $Ru(PPh_3)_3Cl_2$ (Ru-content 10.0 wt. %; Umicore AG & Co KG, Hanau, Germany) are added successively during stirring. After completion, 30 ml of 4M HCl in 1,4-dioxane (Sigma-Aldrich, Munich) are added. The reaction mixture is further stirred for 10 minutes at 90° C.

After that period of time, the reaction mixture is cooled down to 40° C. and 780 ml of the 1,4-dioxane solvent are distilled off in vacuum (about 80 to 90% of the initial quantity). The product precipitates as a brick red powder, is separated from the mother liquor, washed with ethanol and finally dried in vacuum.

| | |
|---|---|
| Yield: | 92% (based on Ru-content). |
| $^{31}$P-NMR ($CD_2Cl_2$): | δ = 29.3 ppm (singlet, product) |
| Purity (based on $^{31}$P-NMR): | 97%. |

EXAMPLE 2

Preparation of $(PCy_3)_2Cl_2Ru(phenylindenylidene)$

A one liter glass reactor with condenser and stirrer is filled with argon and thereafter with 700 ml of 1,4-dioxane. The solvent is heated up to 90° C. Then, 21.5 g (100 mmol) 1,1-diphenyl-2-propyn-1-ol (diphenylpropargylalcohol, GFS) and 90 g (90 mmol) $Ru(PPh_3)_3Cl_2$ (Ru-content 10.0 wt. %; Umicore AG & Co KG, Hanau) are added successively during stirring. After completion, 26 ml of 4M HCl in 1,4-dioxane (Sigma-Aldrich, Munich) are added.

The reaction mixture is further stirred for 10 minutes at 90° C. Thereafter, 61.6 g (210 mmol) tricyclohexylphosphine ($PCy_3$; Aldrich, Munich), dissolved in 50 ml of 1,4-dioxane, are added and the temperature is subsequently cooled down to 25° C. Then, 400 ml of the dioxane solvent (about 60%) are distilled off in vacuum and the product is precipitating from the remaining mother liquor. The precipitate is filtered off and washed with methanol to result in 77 g product.

| | |
|---|---|
| Yield: | 90% (based on Ru-content) |
| $^{31}$P-NMR ($CD_2Cl_2$): | δ = 33.2 ppm (singlet, product) |
| Purity (based on $^{31}$P-NMR): | 95% |

EXAMPLE 3

Preparation of $(PCy_3)(S\text{-}IMes)Cl_2Ru(phenylindenylidene)$

A 500 ml glass reactor with condenser and stirrer is filled with argon and thereafter with 200 ml of 1,4-dioxane. The solvent is heated up to 90° C. Then, 7.3 g (34 mmol) 1,1-diphenyl-2-propyn-1-ol (diphenylpropargylalcohol, GFS) and 30 g (31 mmol) $Ru(PPh_3)_3Cl_2$ (Ru-content 10.0 wt. %; Umicore AG & Co KG, Hanau) are added successively during stirring. After completion, 7.1 ml of 4M HCl in 1,4-dioxane (Sigma-Aldrich, Munich) are added.

The reaction mixture is further stirred for 10 minutes at 90° C. and 4.15 g (10 mmol) tricyclohexylphosphine ($PCy_3$; Aldrich, Munich), dissolved in 50 ml of 1,4-dioxane, are added. Thereafter, residual HCl is removed by distilling off about 170 ml of 1,4-dioxane. After that, 200 ml n-hexane are added and the temperature is adjusted at 70° C. Thereafter, 21.8 g (71 mmol) S-IMes (1,3-bis(mesityl)-imidazolidine-2-ylidene; Aldrich, Munich) are added and the temperature of the reaction mixture is kept for 5 hours at 70° C. Then, 100 ml of the solvent mixture (about 50%) are distilled off in vacuum and the product is precipitating from the remaining mother liquor. The precipitate is filtered off and washed with petrol ether to result in a high purity product.

| | |
|---|---|
| $^{31}$P-NMR ($CD_2Cl_2$): | δ = 27.1 ppm (singlet, product) |
| Purity (based on $^{31}$P-NMR): | 90% |

COMPARATIVE EXAMPLE 1 (CE1)

Preparation of $(PPh_3)_2Cl_2Ru(phenylindenylidene)$ in THF (Prior Art; Ref to Fuerstner et al, *Chem. Eur. J.* 2001, 7, No. 22, 4811-4820)

A one liter glass reactor with condenser and stirrer is filled with argon and thereafter with 800 ml of THF. The solvent is heated up to reflux (65° C.).

Then 29.3 g (140 mmol) of 1,1-diphenyl-2-propyn-1-ol (Diphenylpropargylalcohol, GFS, Germany) and 120 g (120 mmol) of Ru(PPh$_3$)$_3$Cl$_2$ (Ru-content 10.0 wt. %; Umicore AG & Co KG, Hanau) are added successively during stirring. The reaction mixture is further stirred for 2.5 hours at 65° C.

After that period of time, the reaction mixture is cooled down to room temperature and the THF solvent is distilled off in vacuum. The brown solid residue is suspended in n-hexane by thorough agitation for 3 hours. The resulting precipitate is filtered off and dried in vacuum.

| | |
|---|---|
| Yield: | 85% (based on Ru-content) |
| $^{31}$P-NMR (CD$_2$Cl$_2$): | δ = 29.3 ppm (singlet, product) |
| | additional signals: |
| | δ = 28.6 ppm (singlet, Ph$_3$P=O) |
| | δ = 54.0, 47.0, 42.5, 38.5 ppm (side products) |
| Purity (based on $^{31}$P-NMR): | ~80%. |

COMPARATIVE EXAMPLE (CE2)

Preparation of (PPh$_3$)$_2$Cl$_2$Ru(phenylindenylidene) in THF [Prior Art; Ref to Shaffer et al *J. Organomet Chemistry*, 692, 5221-5233 (2007)]

A 100 ml glass flask with condenser and stirrer is filled with argon and thereafter with 40 ml of THF. Then, 1.45 g (10 mmol) of 1,1-diphenyl-2-propyn-1-ol (Diphenylpropargyl-alcohol, GFS, Germany) and 0.625 ml of 4M HCl in 1,4-dioxane (Sigma-Aldrich) as well as 6.0 g (10 mmol) of Ru(PPh$_3$)$_3$Cl$_2$ (Ru-content 10.0 wt. %; Umicore AG & Co KG, Hanau) are added. The mixture is heated up to reflux (65° C.) and stirred under reflux for 1.5 hours.

After that, the reaction mixture is cooled down to room temperature and the THF solvent is distilled off in vacuum. Then, 2-propanol is added and the residue is dispersed in this solvent. The resulting slurry is filtered, the product is washed with 2-propanol and dried in vacuum.

| | |
|---|---|
| Yield: | approx. 80% (based on Ru-content) |
| $^{31}$P-NMR (CD$_2$Cl$_2$): | δ = 29.3 ppm (singlet, product) |
| | additional signals: |
| | δ = 28.6 ppm (singlet, Ph$_3$P=O) |
| | δ = 50.2, 48.4, 48.1, 46.2, 42.0, 40.0 ppm (side products) |
| Purity (based on $^{31}$P-NMR): | 76%. |

The invention claimed is:

1. Method for preparation of a ruthenium-indenylidene carbene catalyst of the formula

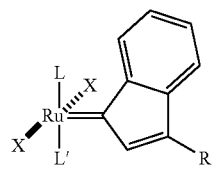

in which
Ru is penta-coordinated in the formal oxidation state +II,
X are anionic ligands,
L or L' are, independent from each other, neutral electron donor ligands,
R is an aryl, phenyl or substituted phenyl group, said method comprising the steps of
  a) reacting the precursor compound Ru(PPh$_3$)$_n$X$_2$ (n=3-4) with a propargyl alcohol derivative of the formula phenyl-C(R)(OH)—C≡C—H in a reaction mixture with a cyclic diether solvent at a temperature in the range of 80 to 130° C.,
  b) optionally adding said neutral electron donor ligand L or L' (with the exemption of PPh$_3$) to the reaction mixture, and
  c) precipitating the resulting ruthenium-indenylidene carbene catalyst from said reaction mixture.

2. Method according to claim 1, wherein the reaction time of step a) is in the range of 1 to 60 minutes.

3. Method according to claim 1, wherein the cyclic diether solvent has a boiling point in the range of 80 to 130° C. at ambient pressure.

4. Method according to claim 1, Wherein the cyclic diether solvent is selected from the group of 1,3-dioxane, 1,4-dioxane, 5-methyl-1,3-dioxane and mixtures thereof.

5. Method according to claim 1, wherein the cyclic diether solvent is 1,4-dioxane.

6. Method according to claim 1, wherein the propargyl alcohol derivative is 1,1-diphenyl-2-propyn-1-ol.

7. Method according to claim 1, wherein reaction step a) is conducted in the presence of an acidic compound.

8. Method according to claim 7, wherein the acidic compound is a protic acid selected from the group of HCl, HBr, H$_2$SO$_4$, HNO$_3$, HBF$_4$, triflic acid (CF$_3$SO$_3$H) and mixtures thereof.

9. Method according to claim 7, wherein the acidic compound is a HCl/1,4-dioxane solution.

10. Method according to claim 1, wherein the Ru precursor compound is Ru(PPh$_3$)$_3$Cl$_2$, having a Ru-content of >9 wt. % Ru.

11. Method according to claim 1, wherein L or L' are selected from the group consisting of PPh$_3$, PCy$_3$, phobane ligands, NHC ligands or mixtures thereof.

12. Method according to claim 11, wherein phobane ligands are added in step b), and are isobutyl-phobanes.

13. Method according to claim 11, wherein NHC ligands are added in step b), and are 1,3-bis(mesityl-imidazoline-2-ylidene ("I-Mes"), 1,3-bis(mesityl)-imidazolidine-2-ylidene ("S-IMes") or 1,3-bis (2,6-di-isopropylphenyl)-imidazoline-2-ylide ("IPr") or mixtures thereof.

14. Method according to claim 1., wherein the neutral electron donor ligands L and/or L' are added simultaneously or sequentially to the reaction mixture.

15. Method according to claim 1, wherein the precipitation step c) is initiated by cooling down the reaction mixture to temperatures in the range of 20 to 40° C.

16. Method according to claim 1, wherein the precipitation step c) is initiated by removing the cyclic diether solvent partly from the reaction mixture.

17. Method according to claim 1, wherein the precipitation step c) is supported by adding at least one solvent with high or low polarity to the reaction mixture.

18. Method according to claim 1, further comprising isolating the ruthenium-indenylidene carbene catalyst from the reaction mixture by a filtration step.

19. A method of synthesizing a modified ruthenium carbene catalyst involving utilizing a ruthenium-indenylidene carbene catalyst obtained by the method according to claim 1, and having a purity of ≥95% (as determined by $^{31}$P-NMR), as a precursor for the synthesis of the modified ruthenium carbene catalyst.

20. Method according to claim 1, wherein the anionic ligands are selected from the group consisting of F', Cl', Br'or I'.

21. Method according to claim 11, wherein phobane ligands are added in step b), and are cyclohexyl-phobanes.

22. Method according to claim 1, wherein the reaction time of step a) is in the range of 1 to 30 minutes.

23. Method according to claim 1, wherein the reaction time of step a) is in the range of 1 to 15 minutes.

24. Method according to claim 1, wherein the cyclic diether solvent has a boiling point in the range of 85° to 120° C. at ambient pressure.

25. Method according to claim 11, wherein the phobane ligands are added in step b), and the added phobane ligands are one of 9-cyclohexyl-9-phospha-bicyclo-[3.3.1.]-nonane or 9-isobutyl-9-phospha-bicyclo-[3.3.1]-nonane.

* * * * *